United States Patent [19]

Iimuro et al.

[11] Patent Number: 4,954,661
[45] Date of Patent: Sep. 4, 1990

[54] PROCESS FOR PREPARING HIGH-PURITY BISPHENOL A

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 321,218

[22] Filed: Mar. 9, 1989

[30] Foreign Application Priority Data

Mar. 11, 1988 [JP] Japan ................................ 63-56335
Mar. 16, 1988 [JP] Japan ................................ 63-60277

[51] Int. Cl.$^5$ ...................... C07C 37/20; C07C 37/84; C07C 39/16
[52] U.S. Cl. ................................. 568/727; 568/724; 568/722; 568/728
[58] Field of Search ................ 568/724, 722, 728, 727

[56] References Cited

U.S. PATENT DOCUMENTS

| | | | |
|---|---|---|---|
| 4,180,683 | 12/1979 | Mitchell | 568/724 |
| 4,209,646 | 6/1980 | Gac et al. | 568/724 |
| 4,354,046 | 10/1982 | Ladewig et al. | 568/724 |
| 4,400,553 | 8/1983 | Aneja | 568/724 |
| 4,400,555 | 8/1983 | Mendiratta | 568/728 |

FOREIGN PATENT DOCUMENTS 1565667 4/1980 United Kingdom ................ 568/724

Primary Examiner—Werren B. Lone
Attorney, Agent, or Firm—Burns, Doane, Swecker & Mathis

[57] ABSTRACT

A method for preparing high-purity bisphenol A which comprises a principal process comprising a first reaction step for reacting phenol with acetone, a first concentration adjusting step, a first crystallization step for precipitating crystals of the adduct of bisphenol A with phenol, a first separation step for separating a solution containing the crystals of the adduct into the crystals and the mother liquor and a phenol removing step for removing phenol from the crystals of the adduct; and a sub-process comprising a second reaction step for reacting p-isopropenylphenol with phenol, a second concentration adjusting step, a second crystallization step, a second separation step for separating a solution containing the second any crystals of the adduct into the second any crystals and the second mother liquor and a cleaving step, the first mother liquor from the principal process being fed to the sub-process and the second any crystals of the adduct from the sub-process being fed to the principal process, is herein provided.

In addition, a method for preparing high-purity bisphenol A which comprises a principal process comprising a first reaction/catalyst removing step for reacting phenol with acetone and removing the catalyst, a crystallization step for precipitating the adduct of bisphenol A with phenol, a solid-liquid separation step for separating the reaction solution into the crystals of the adduct and the mother liquor and a phenol removing step for removing phenol from the adduct crystals; and a sub-process comprising a second reaction/catalyst removing step for reacting p-isopropenylphenol with phenol and removing the catalyst, a second phenol removing step, a distillation step for separating bisphenol A and low boiling and high boiling substances and a cleaving step, the mother liquor from the principal process being fed to the sub-process and the distilled bisphenol A from the sub-process being fed to the principal process, is also herein provided.

10 Claims, 5 Drawing Sheets

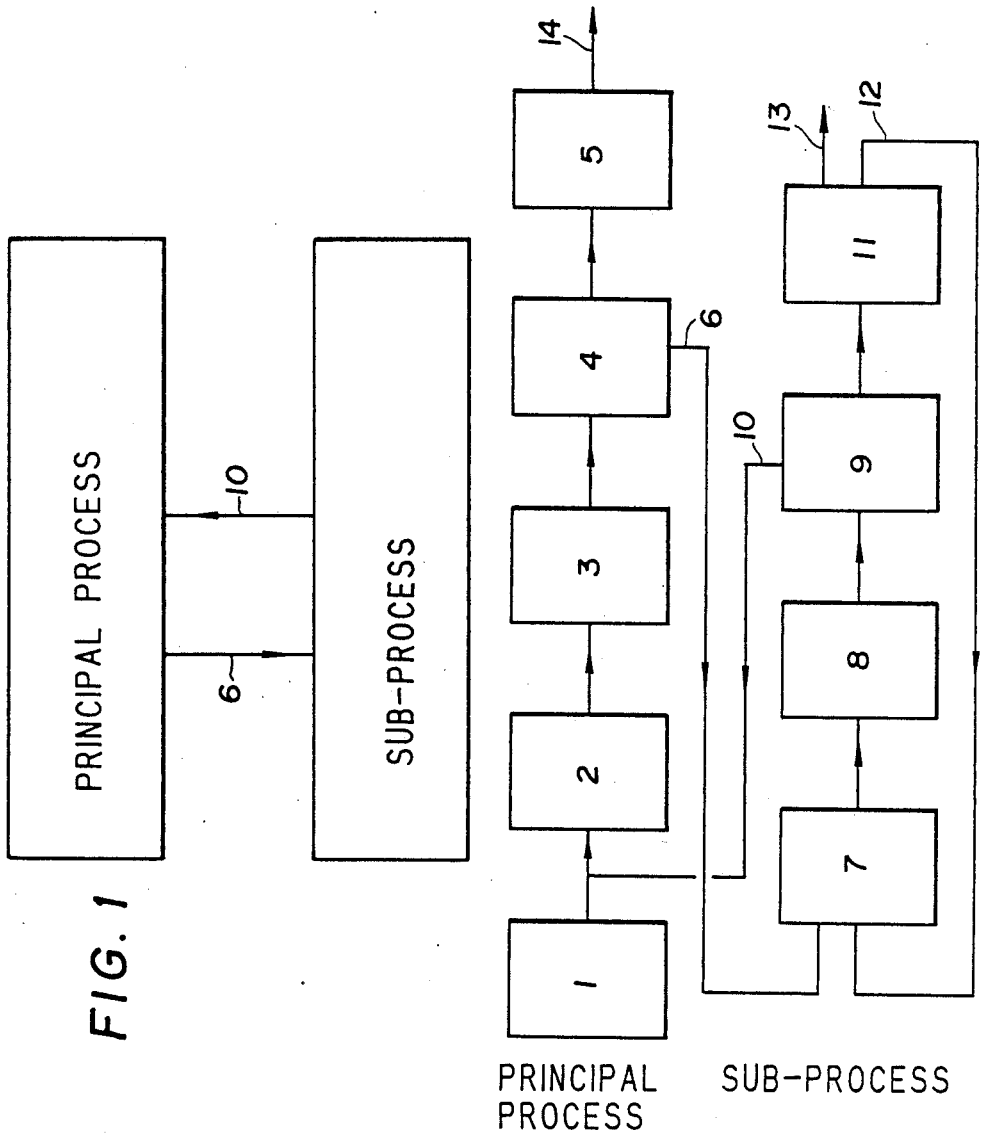

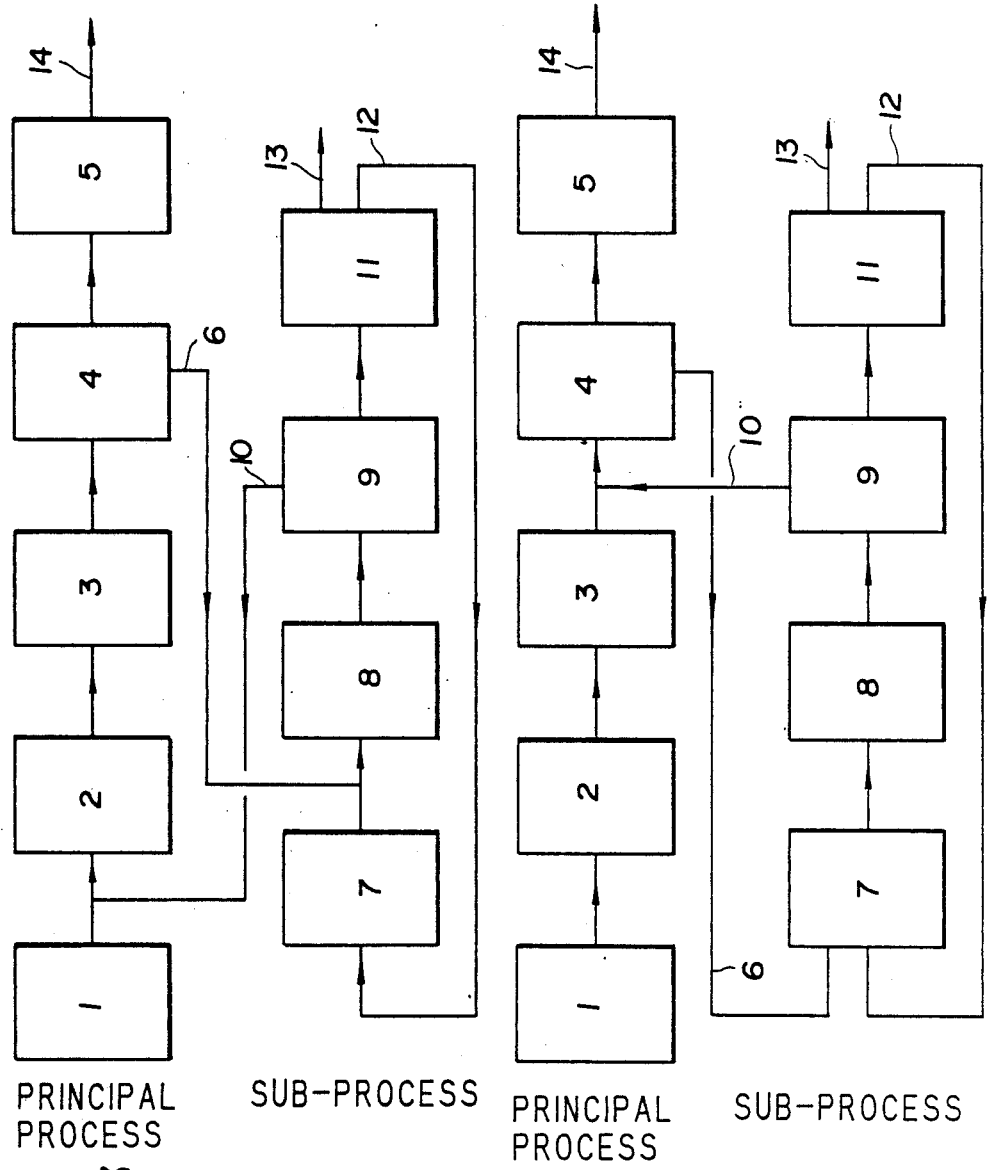

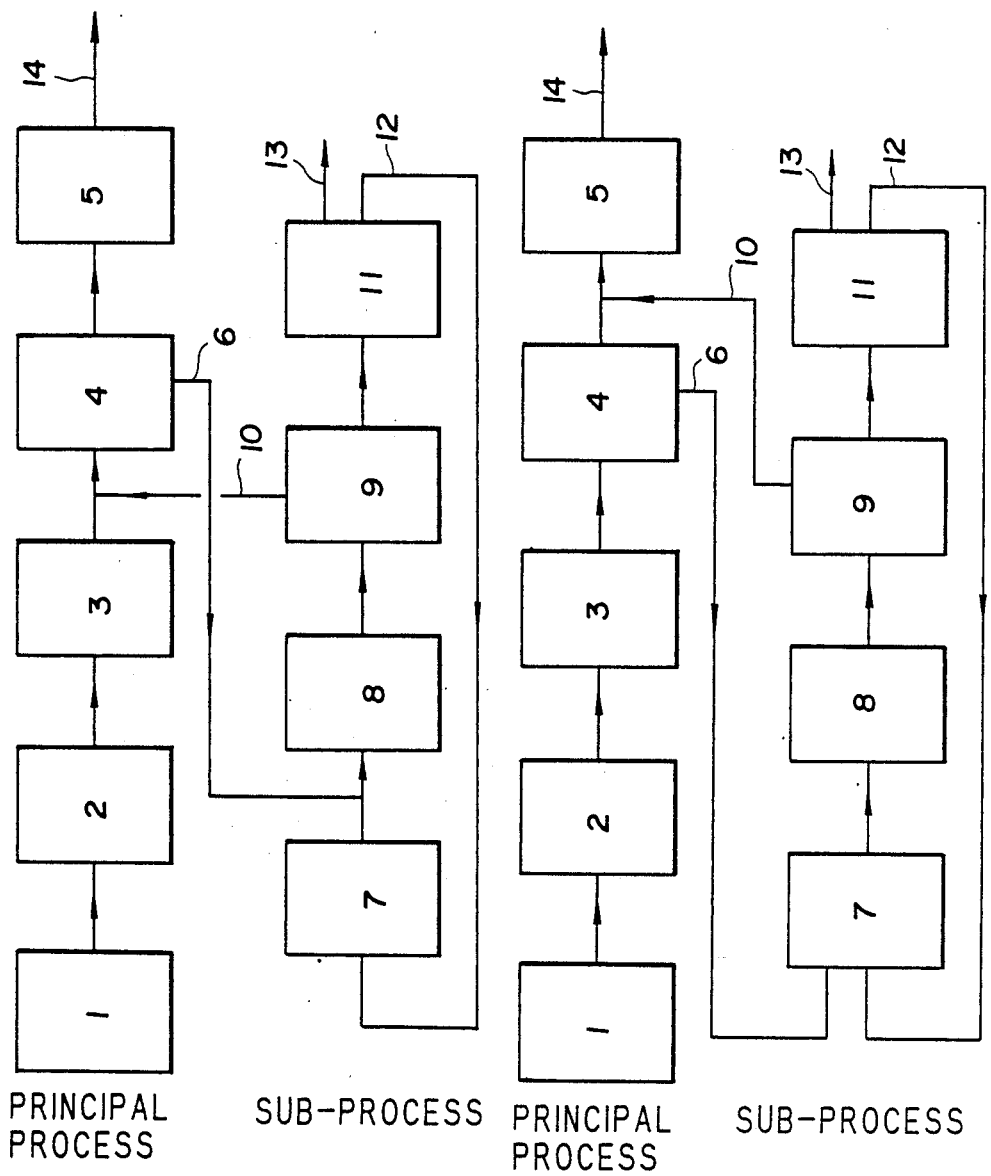

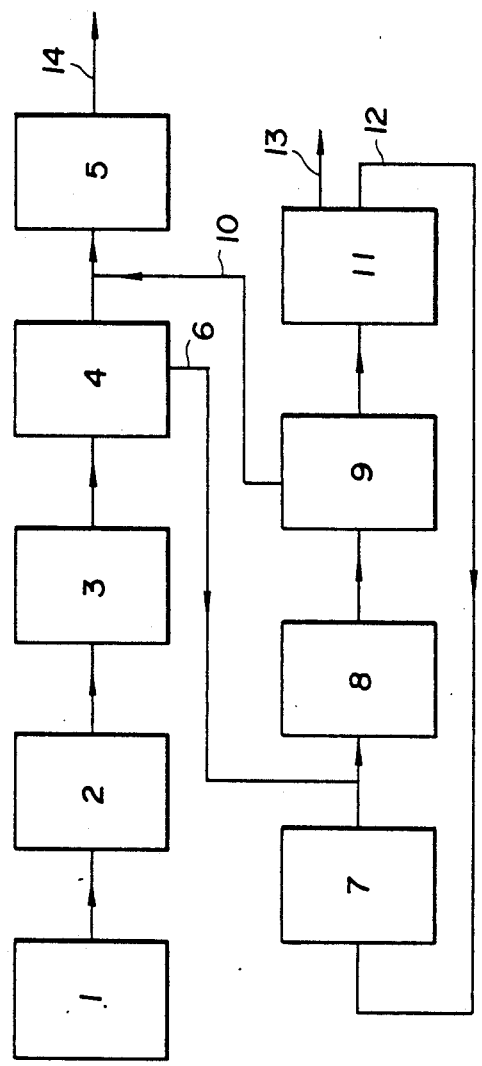
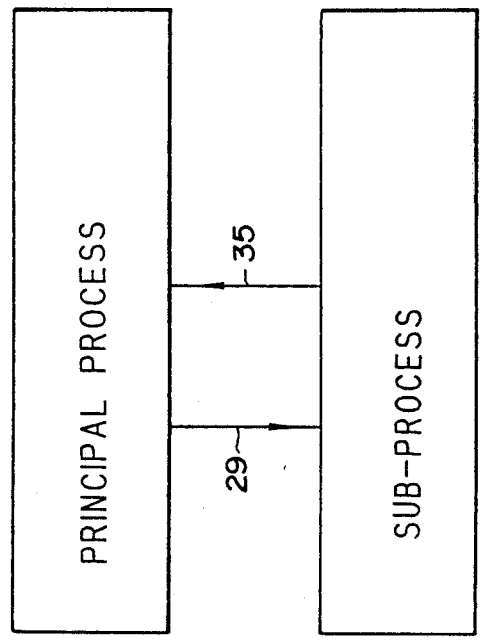

PROCESS FOR PREPARING HIGH-PURITY BISPHENOL A

BACKGROUND OF THE INVENTION

The present invention relates to a process for preparing high-purity 2,2-bis(4-hydroxyphenyl)propane (hereinafter referred to as bisphenol A).

Bisphenol A is used as a raw material for polycarbonate resins and epoxy resins. There is an increasing demand for colorless and high-purity bisphenol A (superior in quality to the conventional ones) which meets the requirements of polycarbonate resins for optical applications.

Bisphenol A is produced by reacting acetone with excess phenol in the presence of an acid catalyst and an optional co-catalyst such as a sulfur compound. The product mixture contains, in addition to the objective bisphenol A, the catalyst used, unreacted acetone, unreacted phenol, water and by-products.

The by-products contain, as major components, 2-(2-hydroxyphenyl)-2-(4-hydroxyphenol)propane (hereunder referred to as "o,p'-isomer") and Dianin's compound. Minor components thereof include trisphenol, polyphenols and coloring substances. They exert adverse effects on the performance of the resins produced from such bisphenol A.

There have been proposed many processes for removing these impurities (by-products) from the objective bisphenol A to obtain high-purity bisphenol A.

One example for obtaining high-purity bisphenol A from such a product mixture comprises the steps of removing the catalyst, unreacted acetone, water and a small amount of phenol from the mixture by vacuum distillation; cooling the residual liquid mixture to crystallize bisphenol A in the form of an adduct with phenol; separating the resulting crystals from the mother liquor containing the by-products; and removing phenol from the adduct to obtain high-purity bisphenol A.

The mother liquor from which the crystals are removed includes bisphenol A in addition to phenol and by-products and, therefore, it is recycled for reuse.

One example of such reuse thereof is to recycle the mother liquor to the reaction system. The o,p'-isomer and trisphenol which are principal components of the by-products exist in the reaction system at a constant equilibrium composition with bisphenol A and, therefore, a part of them may be recovered as bisphenol A. However, Dianin's compound, polyphenols and coloring substances exist in the reaction system as they are or react with the starting phenol or acetone to form high molecular weight substances and these substances remain in the reaction system. This leads to an accumulation of such substances in the reaction system due to the recycle of the mother liquor and in turn impairs the purity and color shade of the adduct.

For this reason, a part of the mother liquor recycled to the reaction system should be purged, but in this case useful bisphenol A would be disposed.

G.B. Pat. No. 1,565,667 and Japanese Pat. Publication No. 55-34779 disclose a method for recovering bisphenol A from the recycled flow of the mother liquor and for removing such coloring substances. According to this method, at least part of the recycled flow of the mother liquor is treated with an adsorbent consisting of a cation exchange resin to remove the coloring substances, prior to recycling it to the reaction system.

The effect attained by such a cation exchange resin as used in the invention disclosed in the foregoing patents can likewise be obtained in cases where other adsorbents are utilized. However, such adsorbents cannot be used continuously without any regeneration, the regeneration requires the steps of washing, drying and removing adsorbed substances (coloring substances) from the wash liquid and further the amount of the mother liquor which can effectively be treated and decolorized with such an adsorbent is not so great. Thus, it is required to frequently exchange the adsorbent. Moreover, not all the impurities present in the mother liquor are converted to bisphenol A and recovered. Therefore, the resulting bisphenol A necessarily contains impurities greater than those in bisphenol A obtained without recycling the mother liquor.

In addition, the recycle of the mother liquor to the reaction system results in the circulation of bisphenol A which has already been formed even if such recycle is performed in any manner. This leads to the substantial reduction in the productivity of the reaction system.

Moreover, U.S. Pat. No. 4,209,646 and Japanese Publication No. 52-46946 disclose a secondary process which comprises removing a part of the phenol in the mother liquor obtained in the principal process to concentrate it, further recovering crystals of the adduct of phenol with bisphenol A, using the recovered adduct or bisphenol A obtained by removing phenol from the adduct to prepare a liquid mixture, and then supplying the liquid mixture to the principal crystallization process. However, in this method, the mother liquor obtained in the secondary process is to be disposed. The mother liquor from the secondary process still contains not only bisphenol A, o,p'-isomer and trisphenol convertable to bisphenol A but also simultaneously contains polyphenols and coloring substances in high proportions. Thus, the mother liquor could not be recycled to any process.

Consequently, according to the conventional method, about 5% of the starting materials with respect to the total amount of bisphenol A product is innevitably disposed.

In G.B. Pat. No. 1,565,667 and Japanese Pat. Publication No. 55-34779, there is disclosed a method comprising treating a part of the residual mother liquor from which bisphenol A has been removed in the form of an adduct with phenol in the presence of an alkaline catalyst to cleave certain components present therein into phenol and p-isopropenylphenol and then recycling the cleavage product to the principal reaction process.

Likewise, U.S. Pat. No. 4,400,555 discloses a method comprising isomerizing a part of the residual mother liquor from which bisphenol A has been removed in the form of an adduct with phenol, or treating a part of the residual mother liquor in the presence of an acid catalyst to cleave certain components present therein into phenol and p-isopropenylphenol, and then isomerizing it and the untreated residual mother liquor, and thereafter recycling the cleavage products to the principal reaction process.

The cleavage reaction of the mother liquor containing o,p'-isomer or by-products conventionally employed is an effective tool for obtaining bisphenol A in a high yield, but it is difficult to prevent bisphenol A from being contaminated with low boiling substances other than phenol and p-isopropenylphenol. Thus, bisphenol A obtained by such a recombination shows purity lower than that of the product prepared from phenol and acetone. Under such circumstances, the yield of bisphenol A can be increased by recycling the cleavage product to the principal process, but on the contrary the load of the purification process increases and the gain due to the increase in yield correspondingly decreases.

SUMMARY OF THE INVENTION

An object of the present invention is to provide a method for preparing high-purity and high quality bisphenol A by recovering, in a high yield, bisphenol A from the mother liquor from which the adduct of bisphenol A with phenol has been separated, simultaneously removing coloring substances and other impurities to reduce the amount thereof, as low as possible, which may be recycled to the principal reaction process thereby increasing the yield and purity of crystals of the adduct produced in the principal process.

The inventors of the present invention have conducted various studies to attain the foregoing object, have found that the object can effectively be achieved by recycling and/or supplying the mother liquor and crystals to specific processes and thus have completed the present invention.

According to the first aspect of the present invention, there is provided a method for preparing bisphenol A comprising a principal process which comprises the steps of (1) reacting phenol with acetone in the presence of an acid catalyst to obtain a first reaction solution, (2) removing a part of the phenol and/or the catalyst and water from the first reaction solution to form a first concentration adjusted solution, (3) cooling the first concentration adjusted solution to obtain a first slurry containing an adduct of bisphenol A with phenol, (4) subjecting the first slurry to solid-liquid separation to form primary crystals and a first mother liquor and (5) removing phenol from the primary crystals to obtain bisphenol A; and a sub-process which comprises the steps of (6) reacting p-isopropenylphenol with phenol in the presence of an acid catalyst to form a second reaction solution, (7) removing a part of the phenol and/or the catalyst and water from the second reaction solution to form a second concentration adjusted solution, (8) cooling the second concentration adjusted solution to obtain a second slurry, (9) subjecting the second slurry to solid-liquid separation to obtain second any crystals and a second mother liquor and (10) treating the second mother liquor to obtain p-isopropenylphenol and phenol, the first mother liquor from the principal process and phenol, the first mother liquor from the principal process being fed to the sub-process and the second any crystals from the sub-process being fed to the principal process.

According to a first aspect of the present invention, a portion of the by-products which are not recovered as bisphenol A are withdrawn from the reaction system without being recycled to any process and, therefore, the objective product is not contaminated with such by-products due to the accumulation thereof. Moreover, since all the portions of the by-products which can be recovered as the objective bisphenol A are returned to the principal process, it is possible to increase the productivity of each process to its maximum level.

According to a second aspect of the present invention, there is provided a method for preparing bisphenol A comprising a principal process which comprises the steps of (a) reacting phenol with acetone in the presence of an acid catalyst and removing the acid catalyst from the resulting mixture to obtain a first phenol solution, (b) cooling the first phenol solution to obtain a slurry containing an adduct of bisphenol A with phenol, (c) subjecting the slurry to solid-liquid separation to obtain crystals of the adduct and a mother liquor and (d) removing phenol from the crystals of the adduct to obtain bisphenol A; and a sub-process which comprises the steps of (e) reacting p-isopropenylphenol with phenol in the presence of an acid catalyst and removing the acid catalyst from the resulting mixture to obtain a second phenol solution, (f) removing phenol from the second phenol solution to obtain crude bisphenol A; (g) separating low boiling and high boiling substances from the crude bisphenol A by distillation to obtain distilled bisphenol A and (h) treating the separated low boiling and high boiling substances to obtain p-isopropenylphenol and phenol, the mother liquor from process (c) of the principal process being fed to the sub-process and the distilled bisphenol A from the sub-process being fed to process (b) of the principal process.

According to the second aspect of the present invention, a portion of the by-products which are not recovered as bisphenol A are withdrawn from the reaction system while recycling the same to each process is minimized and, therefore, the objective product is prevented from being contaminated with such by-products due to the accumulation thereof. Moreover, since all the portions of the by-products which can be recovered as the objective bisphenol A are returned to the principal process, it is possible to increase the productivity of each process to its maximum level.

BRIEF EXPLANATION OF THE DRAWINGS

FIG. 1 is a diagram illustrating the relation between the principal process and the sub-process according to the first aspect of the invention;

FIG. 2 is a diagram showing the first embodiment of the first aspect of the invention;

FIG. 3 is a diagram showing the second embodiment of the first aspect of the invention;

FIG. 4 is a diagram showing the third embodiment of the first aspect of the invention;

FIG. 5 is a diagram showing the fourth embodiment of the first aspect of the invention;

FIG. 6 is a diagram showing the fifth embodiment of the first aspect of the invention;

FIG. 7 is a diagram showing the sixth embodiment of the first aspect of the invention;

FIG. 8 is a diagram illustrating the relation between the principal process and the sub-process according to the second aspect of the invention;

DETAILED DESCRIPTION OF THE INVENTION

Figure 9:
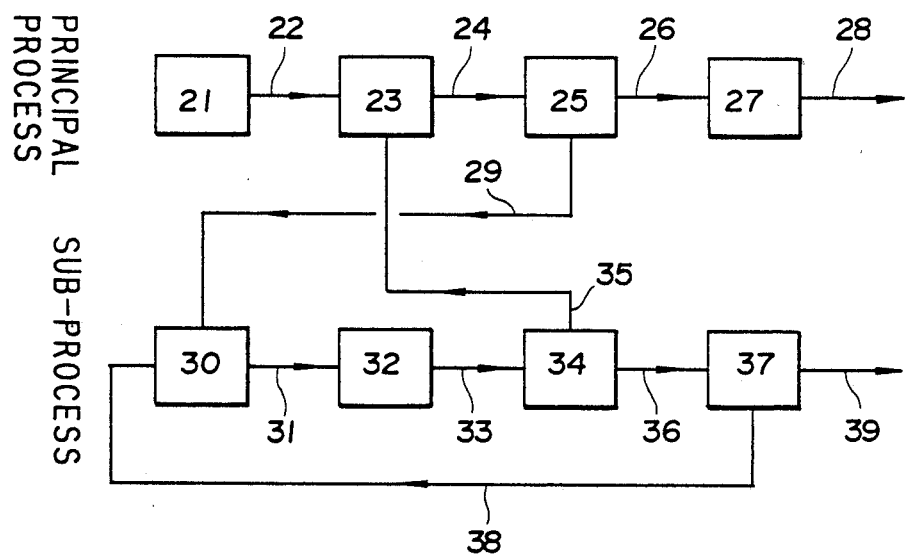
FIG. 9 is a diagram showing the first embodiment of the second aspect of the invention.

The present invention will hereinafter be described in more detail with reference to the attached drawings.

In the embodiments shown in FIGS. 2 to 7, stoichiometrically excess phenol and acetone are introduced into a first reaction step 1. The reaction may be carried out in the presence of a solid acidic catalyst such as a cation exchange resin or an inorganic acid catalyst such as hydrogen chloride.

This reaction is performed at a temperature of 40 to 90° C. During the reaction, bisphenol A and by-products are formed. Such a product mixture is fed to a first concentration adjusting step 2 in which unreacted acetone, water and a part of the phenol are removed. The catalyst is removed in the first reaction step 1 or the first concentration adjusting step 2 depending on whether it is solid or in any other form. In the first concentration adjusting step 2, according to need, the concentration of bisphenol A in the solution is adjusted by removing a part of the phenol from the solution or adding an additional amount of phenol thereto. The concentration adjusted solution thus-obtained is transferred to a first crystallization step 3. The concentration of bisphenol A in the solution to be fed to the crystallizer ranges from 20 to 50% by weight and preferably 30 to 45% by weight. If the concentration of bisphenol A is less than the lower limit, the yield of the product, is lowered while if it is more than the upper limit the, apparent viscosity of the slurry containing the adduct crystals increases and the transport thereof becomes difficult.

The phenol solution fed to the crystallizer is cooled down to 35 to 70° C. to crystallize the adduct of bisphenol A with phenol. The cooling is performed by an external heat exchanger or by removing heat through vacuum evaporation of water added to the crystallizer.

A slurry comprising the crystals of the adduct and the mother liquor is introduced into a first separation step 4 to separate the crystals from the mother liquor. The crystals are optionally washed during or after the separation step and phenol is removed therefrom through a phenol removing step 5 to obtain bisphenol A 14 as the final product.

The first mother liquor 6 from the first separation step 4 is fed to a second reaction step 7 or a second concentration adjusting step (not shown) after it is dehydrated according to need and further a part of the phenol is optionally removed therefrom.

A mixed flow comprising mainly p-isopropenylphenol or its oligomers and phenol or a solution of bisphenol A in phenol obtained from the mixed flow is fed to the second reaction step 7 through a passage 12 to carry out bisphenol A forming reaction and/or conversion of o,p'-isomer and trisphenol to bisphenol A. This recovery reaction may be performed in the presence of an inorganic acid catalyst such as hydrogen chloride or may be performed through a fixed bed of a solid acid catalyst such as a cation exchange resin.

In this respect, it is desirable to concentrate the mother liquor such that the adduct of bisphenol A with phenol is precipitated at the reaction temperature when the recovery reaction is carried out in the presence of an inorganic acid catalyst. The concentration should be effected until a concentrate containing bisphenol A and o,p'-isomer in an amount of 20 to 50% by weight is obtained.

The precipitation of the crystals of the adduct effectively promotes the conversion of o,p'-isomer to bisphenol A. This recovery reaction is in general carried out at 30 to 70° C.

When the recovery reaction is performed through a fixed bed of a solid catalyst such as a cation exchange resin, the reaction must be carried out under conditions such that the crystals of the adduct do not precipitate. Therefore, in this case, the concentration of the mother liquor is not necessary.

When water is used in the crystallization step and/or the separation step of the principal process, it is desirable to partially or completely remove the water present in the mother liquor.

This is because when an inorganic acid such as hydrochloric acid is used, the presence of excess water leads to a reduction of the reaction rate, and the use of a large amount of catalyst is required corresponding to a large amount of water present to hold the reaction rate constant while if a solid catalyst is used, the reaction does not proceed at all. Therefore, the amount of water to be introduced into the second reaction step 7 is desirably restricted to not more than 5% by weight based on the total weight of the reaction mixture.

The catalyst is optionally removed from the product mixture from the second reaction step 7, the mixture is further concentrated, fed to a second crystallization step 8 and cooled therein to precipitate second any crystals of the adduct. The second any crytals 10 are separated from a second mother liquor in a second separation step 9. The second mother liquor contains not only bisphenol A and o,p'-isomer in the same proportions as those in the mother liquor obtained from the first crystallization step 3 but also more concentrated other by-products such as Dianin's compound, trisphenol, polyphenols and coloring substances.

The recovery of bisphenol A from the second mother liquor can be performed by a method comprising additionally concentrating it to obtain crystals; or a method comprising isomerizing o,p'-isomer to bisphenol A and then obtaining bisphenol A or an adduct by distillation or precipitation. However, the bisphenol A recovered in either of these methods contains a large amount of by-products such as Dianin's compound, trisphenol, polyphenols and other coloring substances and thus the accumulation of these impurities cannot be prevented even if such bisphenol A is introduced into any steps mentioned above.

The second mother liquor is optionally concentrated, then fed to a cleaving step 11 wherein it is treated at an elevated temperature in the presence of a basic catalyst and thus recovered as a mixed flow of p-isopropenylphenol and phenol. Most of the coloring substances and a very small amount of unusable portion of the mother liquor are withdrawn from the reaction system through a passage 13.

In accordance with a known method, bisphenol A is regenerated from p-isopropenylphenol and phenol. The resulting bisphenol A is used as the raw material for obtaining the second any crystals of the adduct together with bisphenol A obtained from the first mother liquor 6. Mixing these sources of bisphenol A may be performed before or after the second reaction step. According to one embodiment, a flow of cleaved effluent is fed to the second reaction step 7 (hereafter referred to as "recovery reaction zone") together with the first mother liquor 6 obtained from the principal process, through the passage 12 (which corresponds to claims 2, 4 and 6).

When the recovery reaction zone comprises at least two reactors, the cleaved effluent is desirably fed to the final reactor in order to prevent the conversion of bisphenol A selectively formed from p-isopropenylphenol or its oligomers and phenol to o,p'-isomer.

One of advantages of mixing of the cleaved effluent with the first mother liquor 6 is that p-isopropenylphenol or its oligomers can be diluted.

The recombination of p-isopropenylphenol or its oligomers and phenol to bisphenol A takes place immediately in the presence of an acidic catalyst. Therefore, the reaction of the cleaved effluent alone accompanies an abrupt increase of reaction temperature and as a result, causes the formation of undesirable by-products such as a cyclic dimer of p-isopropenylphenol. When the cleaved effluent and the first mother liquor 6 are mixed together, the reaction proceeds relatively gently, but it proceeds faster than the conversion of o,p'-isomer in the mother liquor to bisphenol A. In addition, the control of the reaction temperature becomes easier and it is not necessary to use an additional amount of phenol for dilution.

According to another embodiment, the first mother liquor 6 is supplied to the second concentration adjusting step in the sub-process (which corresponds to claims 3, 5 and 7). In this case, it is preferred that the second reaction be performed by additionally adding phenol to the cleaved effluent.

In any case, the second reaction is preferably carried out in the presence of phenol of 3 to 10 moles per mole of p-isopropenylphenol. This is because if the amount of phenol is less than the lower limit, a large amount of undesirable by-products such as a cyclic dimer of p-isopropenylphenol are formed while if it is more than the upper limit, the load of the concentration adjusting step is increased and/or the yield in the second crystallization step is lowered.

One of favorable features of the first aspect of the present invention is to recover the second any crystals of the adduct obtained in the second crystallization step 8 as the raw material to be precipitated out in the principal process (which corresponds to claims 2 and 3).

The raw material for the second crystallization step 8 contains by-products present in the raw material to be precipitated out in the principal process in a highly concentrated state. Correspondingly, the second any crystals contain much more impurities compared with those obtained from the principal process.

However, the ratio of impurities to bisphenol A present in the second crystals is lower than that of by-products to bisphenol A present in the product obtained in the first reaction step 1. Therefore, when the second any crystals are recovered in the first concentration adjusting step 2, the ratio of by-products to bisphenol A becomes lower and thus there is obtained crystals having purity higher than those obtained without carrying out such recovery. Thus bisphenol A obtained according to the first aspect of the present invention has a higher purity compared with those prepared according to any conventional commercialized processes.

Another method for recovering second any crystals comprises the step of feeding the crystals to the first separation step 4 (which corresponds to claims 4 and 5). The in-take of impurities by the second any crystals is negligible compared with the amount of those in the mother liquor adhered to the crystals due to the excellent ability of purification achieved during the formation of the adduct. For instance, high-purity bisphenol A can be obtained by subjecting the first crystals to a first separation step in a bath, supplying the second any crystals to the same bath, redispersing them with phenol to form a slurry thereby completely removing the adhered mother liquor.

According to a further method for recovering the second any crystals, they can be recovered in the step 5 for removing phenol in the principal process (which corresponds to claims 6 and 7).

When the second any crystals are recovered in the first concentration adjusting step 2 or the first separation step 4, the load in each process increases and large-sized installations are required. However, when they are recovered in the final step, it is sufficient for the principal process to have an ability for processing bisphenol A produced in the first reaction step.

In the final step, the crystals of the adduct from the principal process and sub-process may be treated simultaneously or separately. When they are treated simultaneously, a smaller sized installation can be used while if they are treated separately, two kinds of bisphenol A which are suitable for two different applications or satisfy different quality requirements can be obtained.

Figure 10:
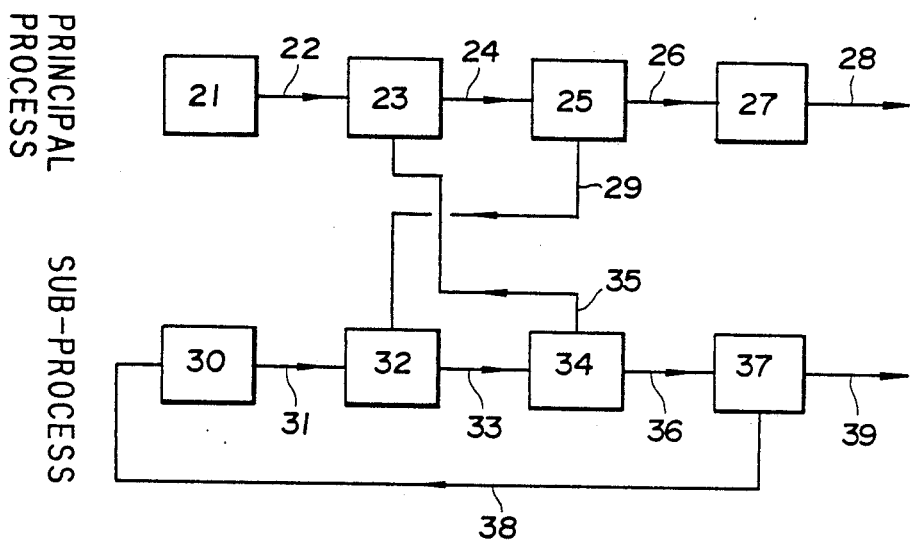
FIG. 10 is a diagram showing the second embodiment of the second aspect of the invention.

In the embodiments shown in FIGS. 9 and 10, stoichiometrically excess phenol and acetone are introduced into a first reaction/catalyst removing step 21. The reaction may be carried out through a fixed bed of a solid catalyst such as a cation exchange resin or in the presence of an inorganic acid catalyst such as hydrochloric acid. The reaction is carried out at a temperature of 40 to 90° C. and provides bisphenol A and by-products.

The removal of the catalyst is not necessary when the fixed bed of a solid catalyst such as a cation exchange resin is used and in this case, unreacted acetone and water generated are removed by a means such as vacuum distillation.

When hydrochloric acid is used as a catalyst, hydrochloric acid, unreacted acetone and water are likewise removed by a means such as vacuum distillation.

After removing the catalyst, a first phenol solution 22 is fed to a crystallization step 23 in which bisphenol A in the solution is crystallized directly or after adjusting the concentration of bisphenol A by removing a part of the phenol from the solution or adding an additional amount of phenol thereto. The concentration of bisphenol A in the solution to be fed to the crystallizer ranges from 20 to 50% by weight and preferably 30 to 45% by weight.

If the concentration of bisphenol A is less than the lower limit, the yield of the product is lowered while if it is more than the upper limit, the apparent viscosity of the slurry containing adduct crystals increases and the transport thereof becomes difficult.

The phenol solution fed to the crystallizer is cooled down to 35 to 70° C. to crystallize the adduct of bisphenol A and phenol. The cooling is performed by an external heat exchanger or by removing heat through vacuum evaporation of water added to the crystallizer.

A slurry 24 composed of the crystals of the adduct and the mother liquor is fed to a solid-liquid separation step 25 in which it is separated into the crystals 26 and the mother liquor 29.

The crystals are optionally washed during the separation step or after the separation step and then fed to a phenol removing step 27.

Phenol is removed by means such as vacuum distillation and thus bisphenol A 28 is obtained as the final product.

The separated mother liquor 29 is optionally dehydrated prior to sending it to a second reaction/catalyst removing step 30 or a phenol removing step 32.

In addition, a part of the mother liquor 29 may be returned to the crystallization step 23 directly or after adjusting the concentration of bisphenol A therein. This makes it possible to use small-sized installations in the sub-process.

A mixture 38 principally comprised of p-isopropenylphenol or its oligomers and phenol is fed to the second reaction/catalyst removing step 30 wherein bisphenol A is produced.

When the mother liquor 29 to be fed to the sub-process is mixed with the mixture 38 and introduced into the second reaction/catalyst removing step 30 as a raw material, the conversion of a part of the o,p'-isomer and trisphenol to bisphenol A occurs in addition to the foregoing reaction.

The reaction may be performed in the presence of an inorganic acid catalyst such as hydrochloric acid or through a fixed bed of a solid catalyst such as a cation exchange resin.

When the reaction is carried out in the presence of an inorganic acid catalyst, it is desirable to concentrate the mother liquor such that the crystals of the adduct of bisphenol A and phenol are precipitated at the reaction temperature. This is because the precipitation of the crystals of the adduct effectively promotes the conversion of o,p'-isomer to bisphenol A. The concentration is desirably performed generally at a temperature of 30 to 70° C. until the concentration of bisphenol A and o,p'-isomer in the concentrated mother liquor becomes 20 to 50% by weight.

When the reaction is performed through a fixed bed of a solid catalyst such as a cation exchange resin, it must be carried out under conditions such that the adduct never crystallizes and, therefore, it is not necessary to concentrate the mother liquor in this case.

When water is used in the crystallization step and/or the solid-liquid separation step of the principal process, it is desirable to partially or completely remove the water present in the mother liquor. This is because if an inorganic acid such as hydrochloric acid is used as the catalyst, the presence of excess water leads to a reduction of the reaction rate while if a solid acid catalyst such as a cation exchange resin is used as the catalyst, the reaction cannot proceed at all.

Therefore, it is desirable that the amount of water to be introduced into the second reaction/catalyst removing step 30 be not more than 5% by weight based on the total weight of the raw material.

One of advantages attained by admixing the mixture 38 of p-isopropenylphenol or its oligomers and phenol and the mother liquor 29 is that p-isopropenylphenol or the oligomer thereof can be diluted.

Since the formation of bisphenol A from p-isopropenylphenol or its oligomers and phenol occurs immediately in the presence of an acid catalyst, the reaction of the mixture 30 alone accompanies an abrupt increase of reaction temperature and as a result, forms undesirable by-products such as a cyclic dimer of p-isopropenylphenol. Whereas, the reaction gently proceeds by admixing the mixture with the mother liquor and thus the control of the reaction becomes easier.

The molar ratio of phenol to p-isopropenylphenol is preferably not less than 3:1 provided that in particular if an inorganic acid catalyst is used, it is preferably not more than 10:1. If the ratio is less than 3:1, in other words if the amount of phenol is lower than the predetermined level, by-products such as a cyclic dimer of p-isopropenylphenol are substantially formed, while if the amount of phenol is excessively large, the conversion of o,p'-isomer to bisphenol A does not proceed as already explained above.

Thus, in order to control the molar ratio of phenol to p-isopropenylphenol, a part of the mother liquor to be fed to the sub-process may be used in the reaction and the balance thereof may be fed to a phenol removing step 32.

The removal of the catalyst is carried out in the manner similar to the principal process.

The resulting second phenol solution 31 is fed to the phenol removing step 32 in which phenol is removed by a means such as vacuum distillation.

Then, the crude bisphenol A 33 is distilled in a distillation step 34 to remove low boiling and high boiling substances and to thus obtain distilled bisphenol A 35 and a mixture 36 of the low boiling and high boiling substances.

As methods for distillation there may be listed, for instance, a method comprising the steps of distilling, in order, low boiling substances, bisphenol A and then high boiling substances; and a method comprising distilling off low boiling substances and bisphenol A to remove high boiling substances and then distilling off the low boiling substances to obtain bisphenol A. However, the former causes heat decomposition of the high boiling substances during separations of the same and the bisphenol A fraction is possibly contaminated with such decomposition products and, therefore, the latter is preferably employed.

Examples of distillation apparatuses include column type distillators and thin film type distillators.

When the high boiling substances are removed, any apparatuses for distillation may be used so far as they can prevent the entrainment of droplets since the difference between the boiling points of the high boiling substances and other components of the crude bisphenol A is large. However, when the low boiling substances are removed from bisphenol A, a rectifying column should be employed since the difference between the boiling points of the same and bisphenol A is small.

The distilled bisphenol A 35 is fed to the principal process and is fed to the crystallization step 23 together with the first phenol solution.

The mixture 36 of the high boiling and low boiling substances is fed to a cleaving step 37 wherein the mixture is heated to an elevated temperature in the presence of a basic or acidic catalyst and then the resulting mixture 38 of p-isopropenylphenol and phenol is recovered. A mixture 39 of most of the coloring substances and a very small amount of unusable portion is removed from the system.

According to a further embodiment, the mother liquor 29 fed to the sub-process is supplied to the phenol removing step 32.

In this case, it is preferred to feed the mixture of p-isopropenylphenol or its oligomers and phenol to the second reaction/catalyst removing step 30 after adjusting the ratio of phenol to p-isopropenylphenol so as to fall within the range of 3:1 to 10:1 by adding phenol.

One of favorable characteristics of the second aspect of the invention is to recover distilled bisphenol A as the raw material for the crystallization in the principal process.

Crude bisphenol A obtained by removing phenol in the sub-process contains by-products to be present in the raw material from the principal process in the highly concentrated state. On the contrary, the proportion of impurities relative to bisphenol A present in the distilled bisphenol A is lower than that of the impurities relative to bisphenol A prepared according to the reaction in the principal process. Therefore, when the distilled bisphenol A is recovered in the crystallization step of the principal process, such a proportion becomes lower and the resulting crystals have a higher purity compared with the crystal obtained without such recovery of bisphenol A.

Thus, bisphenol A obtained according to the first and second aspects of the present invention shows a higher purity compared with those obtained according to any known commercialized methods.

The present invention will hereinafter be explained in more detail with reference to the following Examples. In the following Examples, the term "%" means "% by weight" unless otherwise specified.

EXAMPLE 1

Phenol (750 g) and acetone 75 g) were admixed and the reaction was performed at 55° C. for 8 hours while blowing hydrogen chloride into the mixture. Then, the product mixture was heated under reduced pressure to remove hydrochloric acid and water. The product obtained after removing hydrochloric acid contained 36.8% of bisphenol A, 0.8% of o,p'-isomer and 1.1% of other impurities. The product free of hydrochloric acid was cooled from 90 to 45° C. to crystallize the adduct, followed by separating the crystals with a centrifugal filter, washing the crystals with an equivalent amount of phenol to obtain 300 g of the crystals of the adduct.

The crystals were melted and fed to a distillation column, followed by distilling at 15 Torr, 170° C. to remove most of the phenol and completely removing the residual phenol in the bisphenol A withdrawn from the bottom of the column by steam stripping to recover 210 g of bisphenol A as the final product. Hazen color of a 50% alcoholic solution of the resulting bisphenol A was APHA 10 and the freezing point thereof was 156.7° C. This indicates that the resulting bisphenol A has a sufficient purity and can be used as a raw material for optical polycarbonate resins.

The bisphenol A thus-obtained contained 0.1% of o,p'-isomer and 0.2% of other impurities.

The mother liquor separated with the centrifugal filter and the wash phenol were combined together and phenol was removed from the mixture at a reduced pressure to thus recover 280 g of a bottom liquid containing 30% of bisphenol A. The bottom liquid contained 2.1% of o,p'-isomer and 3.4% of other impurities.

The solution was cooled to precipitate secondary crystals and then the crystals were separated with the centrifugal filter.

The yield of the second any crystals was 85 g and the crystals contained 0.8% of o,p'-isomer and 1% of other impurities. The second mother liquor contained 25 g of bisphenol A, 5 g of o,p'-isomer and 9 g of other impurities.

The second mother liquor was heated at a reduced pressure to remove phenol, followed by adding 0.1 g of sodium hydroxide to the resulting residue and treating it at 240° C. and 3 mm Hg. There was obtained 35 g of a cleaved effluent which is mainly composed of phenol and p-isopropenylphenol.

EXAMPLE 2

According to the same procedures as in Example 1, 1,800 g of a product mixture free of hydrochloric acid was obtained. To the product there was added 85 g of the second any crystals obtained in Example 1 to form a liquid mixture for crystallization.

The raw material contained 40% of bisphenol A, 0.8% of o,p'-isomer and 1.2% of other impurities.

The mixture was cooled to 45° C. to precipitate crystals of the adduct, the crystals were separated with the centrifugal filter and washed with an equivalent amount of phenol to thus obtain 360 g of the crystals. The bisphenol A isolated from the crystals contained 0.09% of o,p'-isomer and 0.2% of other impurities. Hazen color of a 50% alcoholic solution of the bisphenol A thus-obtained was APHA 10 and the freezing point thereof was 156.7° C.

To a mixture of the mother liquor separated with the centrifugal filter and the wash phenol there was added the cleaved effluent obtained in Example 1.

To the mixture there was added 50 g of a cation exchange resin (available from Roh & Haas Co., Ltd. under the trade name of Amberlist 15) and the mixture was treated at 50° C. for two hours. The product of the recovery reaction was filtered to remove the catalyst used and phenol was removed at a reduced pressure to obtain 380 g of a 35% bisphenol A solution.

The solution contained 1.8% of o,p'-isomer and 2.6% of other impurities. The solution was cooled to precipitate second any crystals and the crystals were separated with the centrifugal filter. The secondary crystals contained 0.7% of o,p'-isomer and 0.8% of other impurities and the yield thereof was 135 g.

The second mother liquor was treated according to the same manner as in Example 1 and thus 52 g of a cleaved effluent was obtained.

EXAMPLE 3

The same procedures as in Example 2 were repeated 10 times. 280 g of bisphenol A was recovered from a product mixture obtained by mixing 750 g of phenol and 75 g of acetone and reacting the mixture while blowing hydrogen chloride thereinto.

During the reaction, o,p'-isomer was formed in an amount of 2% relative to bisphenol A and 3% of other impurities were also formed.

To the product mixture from which hydrochloric acid had been removed there was added 170 g of the secondary crystals of the adduct obtained from the mother liquor in the preceeding process to thus form a liquid mixture and the liquid mixture was cooled to precipitate crystals of the adduct.

After washing the crystals with phenol, phenol in the crystals was removed at a reduced pressure to obtain 280 g of bisphenol A.

Hazen color of a 50% alcoholic solution of the bisphenol A thus-prepared was APHA 4 and the freezing point thereof was 156.8° C.

The resulting bisphenol A only included 0.04% of o,p'-isomer and 0.1% of other impurities.

EXAMPLE 4

Phenol was removed from the second any crystals obtained in the same manner as in Example 1 to recover bisphenol A. The resulting bisphenol A included 1.1% of o,p'-isomer and 1.4% of other impurities. Hazen color of a 50% alcoholic solution of the bisphenol A thus-prepared was APHA 25 and the freezing point thereof was 156.6° C.

EXAMPLE 5

Phenol (750 g) and acetone (75 g) were admixed and the mixture was reacted with one another at 55° C. for 8 hours with blowing hydrogen chloride into the mixture.

Then, the resulting product mixture was heated at a reduced pressure to remove hydrochloric acid and water generated.

The resulting product mixture from which hydrochloric acid had been removed included 36.8% of bisphenol A, 0.8% of o,p'-isomer and 1.0% of other impurities.

Then, the product mixture free of hydrochloric acid was cooled down to 45° C. to precipitate crystals of the adduct followed by separating the crystals with the centrifugal filter, washing the crystals with an equivalent amount of phenol to thus obtain 319 g of the crystals of the adduct.

The crystals of the adduct were treated at 170° C. and a pressure of 45 mm Hg to distill off most of the phenol and the residual phenol was completely removed by steam stripping to recover 225 g of bisphenol A.

The resulting bisphenol A included 0.1% of o,p'-isomer and 0.2% of other impurities, Hazen color of a 50% alcoholic solution of the bisphenol A thusprepared was APHA 10 and the freezing point thereof was 156.7° C.

On the other hand, the mother liquor separated with the centrifugal filter and the wash phenol were combined together and treated at 170° C. and a pressure of 15 mm Hg to remove phenol.

The yield of the resulting crude bisphenol A was 83 g and the crude bisphenol A included 82.7% of bisphenol A, 7.5% of o,p'-isomer and 9.0% of other impurities.

Then, the crude bisphenol A was distilled using an apparatus equipped with a column packed with McMahon packings having a diameter of 15 mm and a height of 250 mm to distill off low boiling point substances and bisphenol A.

At this time, the temperature of the top of the column was 195° C., that of the still pot was 225° C. and the pressure was 3 mm Hg.

Then, the distillate was charged into an apparatus similar to that used above and the low boiling substances were distilled off at a temperature of the top of the column of 180° C., a temperature of the still pot of 200° C. and a pressure of 4 mm Hg.

The yield of the distilled bisphenol A obtained from the still pot was 63 g and the bisphenol A included 1% of o,p'-isomer and 1.3% of other impurities.

The mixture of the low boiling and high boiling substances included 7 g of bisphenol A, 5 g of o,p'-isomer and 7 g of other impurities.

Then, 0.05 g of sodium hydroxide was added to the mixture and the cleavage reaction was performed at 240° C. and 10 mm Hg.

As a result, a distillate mainly composed of phenol and p-isopropenylphenol was obtained.

EXAMPLE 6

A product free of hydrochloric acid (800 g) was obtained in the same manner as in Example 5. To this product there was added 63 g of the distilled bisphenol A obtained in Example 5 to form a liquid mixture for crystallization. The raw material included 41.3% of bisphenol A, 0.8% of o,p'-isomer and 1.0% of other impurities.

This phenol solution was treated according to the same manner as in Example 5 to thus obtain 398 g of the crystals of the adduct.

The bisphenol A obtained after removing phenol included 0.09% of o,p'-isomer and 0.2% of other impurities, Hazen color of a 50% alcoholic solution of the bisphenol A was APHA 10.

To a mixture of the mother liquor obtained by the separation with the centrifugal filter and the wash phenol there was added the cleaved effluent obtained in Example 5 and the resulting mixture was treated with 50 g of a cation exchange resin (available from Rohm & Haas Co., Ltd. under the trade name of Amberlist 15) at 50° C. for two hours.

The resin was filtered off from the product mixture of the recovery reaction and phenol was removed in the same manner as in Example 5 to obtain 106 g of crude bisphenol A.

The crude bisphenol A contained 84.5% of bisphenol A, 6.7% of o,p'-isomer and 8.2% of other impurities.

Then, according to the same manner as in Example 5, low boiling and high boiling substances were separated from bisphenol A.

The yield of the resulting distilled bisphenol A was 83 g and the bisphenol A included 0.8% of o,p'-isomer and 1.1% of other impurities.

Moreover, the yield of the mixture of low boiling and high boiling substances was 23 g. This mixture was treated with sodium hydroxide in the same manner as in Example 5 to obtain 19 g of a cleaved distillate.

EXAMPLE 7

According to the same procedures as in Example 6, the distilled bisphenol A obtained in the preceding process was added to 800 g of a product free of hydrochloric acid to form a raw material for crystallization and bisphenol A was recovered.

The mother liquor obtained in the above procedure was mixed with the cleaved effluent obtained in the preceding process and the mixture was used as the raw material for the recovery reaction.

The foregoing procedures were repeated 10 times.

The resulting bisphenol A included 0.04% of o,p'-isomer and 0.1% of other impurities. Hazen color of a 50% alcoholic solution thereof was APHA 5. In addition, the freezing point of the bisphenol A was 156.8° C. Thus, the resulting bisphenol A was extremely pure.

EXAMPLE 8

The same procedures as in Example 7 were repeated to obtain bisphenol A except that the mother liquor obtained in the principal process was treated in the phenol removing step in the sub-process, in other words in the process for obtaining crude bisphenol A, that phenol which was twice as much as the amount of the cleaved effluent was used and that 5 g of Amberlist 15 was used as the catalyst.

The bisphenol A finally obtained included 0.04% of o,p'-isomer and 0.1% of other impurities. Hazen color of a 50% alcoholic solution thereof was APHA 5 and the freezing point thereof was 156.8° C.

Since the method of the present invention comprises the foregoing steps explained above, most of the by-products which pass through a part of the principal process and sub-process only once are subjected to a cleaving reaction. Therefore, the accumulation of the by-products due to the recycling thereof is not caused at all or is restricted to its minimum level and hence the contamination in each step is also restricted to its minimum level. In addition, the recycling of impurities is restricted and, therefore, the productivity of each step can be increased to its maximum level.

Moreover, phenol and p-isopropenylphenol are recovered from a part of the trisphenol and polyphenols and these compounds are converted to bisphenol A in the sub-process. Therefore, bisphenol A greater than the total amount of bisphenol A and o,p'-isomer present in the first mother liquor can be recovered in the sub-process and returned to the principal process. Thus, the amount of bisphenol A obtained as the final product according to the present invention can be increased to a level greater than the amount simply produced in the principal process.

What is claimed is:

1. A method for preparing high-purity bisphenol A comprising a principal process which comprises the steps of (1) reacting phenol with acetone at a temperature of 40 to 90° C. of an acid catalyst which catalyzes the reaction of phenol and acetone to form bisphenol A to obtain a first reaction solution, (2) removing a part of the phenol and/or the catalyst and water from the first reaction solution to form a first concentration adjusted solution, (3) cooling the first concentration adjusted solution to obtain a first slurry containing an adduct of bisphenol A with phenol, (4) subjecting the first slurry to solid-liquid separation to form primary crystals and a first mother liquor and (5) removing phenol from the first crystal to obtain bisphenol A; and a sub-process which comprises the steps of (6) reacting p-isopropenylphenol with phenol in the presence of an acid catalyst to form a second reaction solution, (7) removing a part of the phenol and/or the catalyst and water from the second reaction solution to form a second concentration adjusted solution, (8) cooling the second concentration adjusted solution to obtain a second slurry, (9) subjecting the second slurry to solid-liquid separation to obtain secondary crystals and a second mother liquor and (10) treating the second mother liquor to obtain p-isopropenylphenol and phenol, the first mother liquor from the principal process being fed to the sub-process and the secondary crystals from the sub-process being fed to the principal process.

2. A method for preparing bisphenol A according to claim 1 wherein the first mother liquor from the principal process is fed to the reaction step in the sub-process and the secondary crystals from the sub-process are fed to the concentration adjusting step in the principal process.

3. A method for preparing bisphenol A according to claim 1 wherein the first mother liquor from the principal process is fed to the concentration adjusting step in the sub-process and the secondary crystals from the sub-process are fed to the concentration adjusting step in the principal process.

4. A method for preparing bisphenol A according to claim 1 wherein the first mother liquor from the principal process is fed to the reaction step in the sub-process and the secondary crystals from the sub-process are fed to the separation step in the principal process.

5. A method for preparing bisphenol A according to claim 1 wherein the first mother liquor from the principal process is fed to the concentration adjusting step in the sub-process and the secondary crystals from the sub-process are fed to the separation step in the principal process.

6. A method for preparing bisphenol A according to claim 1 wherein the first mother liquor from the principal process is fed to the reaction step in the sub-process and the secondary crystals from the sub-process are fed to the phenol removing step in the principal process.

7. A method for preparing bisphenol A according to claim 1 wherein the first mother liquor from the principal process is fed to the concentration adjusting step in the sub-process and the secondary crystals from the sub-process are fed to the phenol removing step in the principal process.

8. A method for preparing high-purity bisphenol A comprising a principal process which comprises the steps of (a) reacting phenol with acetone at a temperature of 40 to 90° C. in the presence of an acid catalyst which catalyzes the reaction of phenol and acetone to form bisphenol A and removing the acid catalyst from the resulting mixture to obtain a first phenol solution, (b) cooling the first phenol solution to obtain a slurry containing an adduct of bisphenol A with phenol, (c) subjecting the slurry to solid-liquid separation to obtain crystals of the adduct and a mother liquor and (d) removing phenol from the crystals of the adduct to obtain bisphenol A; and sub-process which comprises the steps of (e) reacting p-isopropenylphenol with phenol in the presence of an acid catalyst and removing the acid catalyst from the resulting mixture to obtain a second phenol solution, (f) removing phenol from the second phenol solution to obtain crude bisphenol A; (g) separating low boiling and high boiling substances from the crude bisphenol A by distillation to obtain distilled bisphenol A and (h) treating the separated low boiling and high boiling substances to obtain p-isopropenylphenol phenol and phenol, the mother liquor from step (c) of the principal process being fed to the sub-process and the distilled bisphenol A from the sub-process being fed to step (b) of the principal process.

9. A method for preparing bisphenol A according to claim 8 wherein the mother liquor from the principal process is fed to step (e) as a raw material for the reaction in the sub-process.

10. A method for preparing bisphenol A according to claim 8 wherein the mother liquor from the principal process is fed to step (f) in the sub-process.

* * * * *